United States Patent [19]

Sacristan et al.

[11] Patent Number: 5,158,083

[45] Date of Patent: Oct. 27, 1992

[54] MINIATURE PCO$_2$ PROBE FOR IN VIVO BIOMEDICAL APPLICATIONS

[75] Inventors: Emilio Sacristan, Worcester; Albert Shahnarian; Robert A. Peura, both of Princeton, all of Mass.

[73] Assignee: Mountpelier Investments, S.A., Vaduz, Liechtenstein

[21] Appl. No.: 425,490

[22] Filed: Oct. 23, 1989

[51] Int. Cl.$^5$ ............................................. A61B 5/00
[52] U.S. Cl. ................................... 128/635; 128/632
[58] Field of Search ............... 128/632, 635, 637, 639, 128/662.03, 662.06, 692

[56] References Cited

U.S. PATENT DOCUMENTS

| | | | |
|---|---|---|---|
| 4,244,713 | 1/1981 | Goodwin | 128/632 |
| 4,741,343 | 5/1988 | Bowman et al. | 128/635 |
| 4,834,101 | 5/1989 | Collison et al. | 128/635 |
| 4,836,907 | 6/1989 | Pedersen | 128/635 |
| 4,901,727 | 2/1990 | Goodwin | 128/632 |

FOREIGN PATENT DOCUMENTS

| | | |
|---|---|---|
| 2023584 | 11/1970 | Fed. Rep. of Germany . |
| 0015075 | 9/1980 | United Kingdom . |
| 0039136 | 11/1981 | United Kingdom . |
| 0039243 | 11/1981 | United Kingdom . |

OTHER PUBLICATIONS

Brantigan et al., "A Non-Thrombogenic Diffusion Membrane for Continuous In Vivo Measurement of Blood Gases by Mass Spectroscopy", Journal of Applied Physiology, vol. 28, No. 3, Mar. 1970.

Primary Examiner—Peter A. Aschenbrenner
Attorney, Agent, or Firm—Harness, Dickey & Pierce

[57] ABSTRACT

The pCO$_2$ probe has a miniaturized glass bulb pH sensor concentrically arranged in a flexible, noncollapsible hollow tube. A silicone end cap is expanded in a freon solvent and placed over the end of the tube while the freon evaporates, returning the end cap to its normal contracted size where it forms a tight elastic fit. The pH sensor includes an internal electrode and an outer electrode is concentrically wrapped about the glass bulb so the electrodes are in close proximity. The glass bulb and the chamber defined by the tube walls and silicone membrane are both filled with suitable electrolytes of sufficient volume to minimize air bubbles. Without air bubbles, the electrodes remain emersed in the respective electrolytes regardless of the physical orientation of the probe.

15 Claims, 3 Drawing Sheets

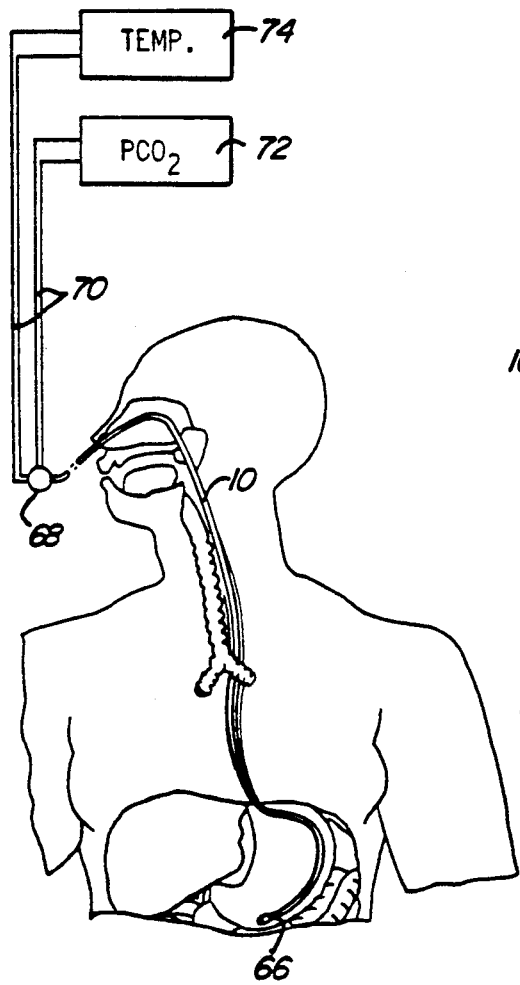
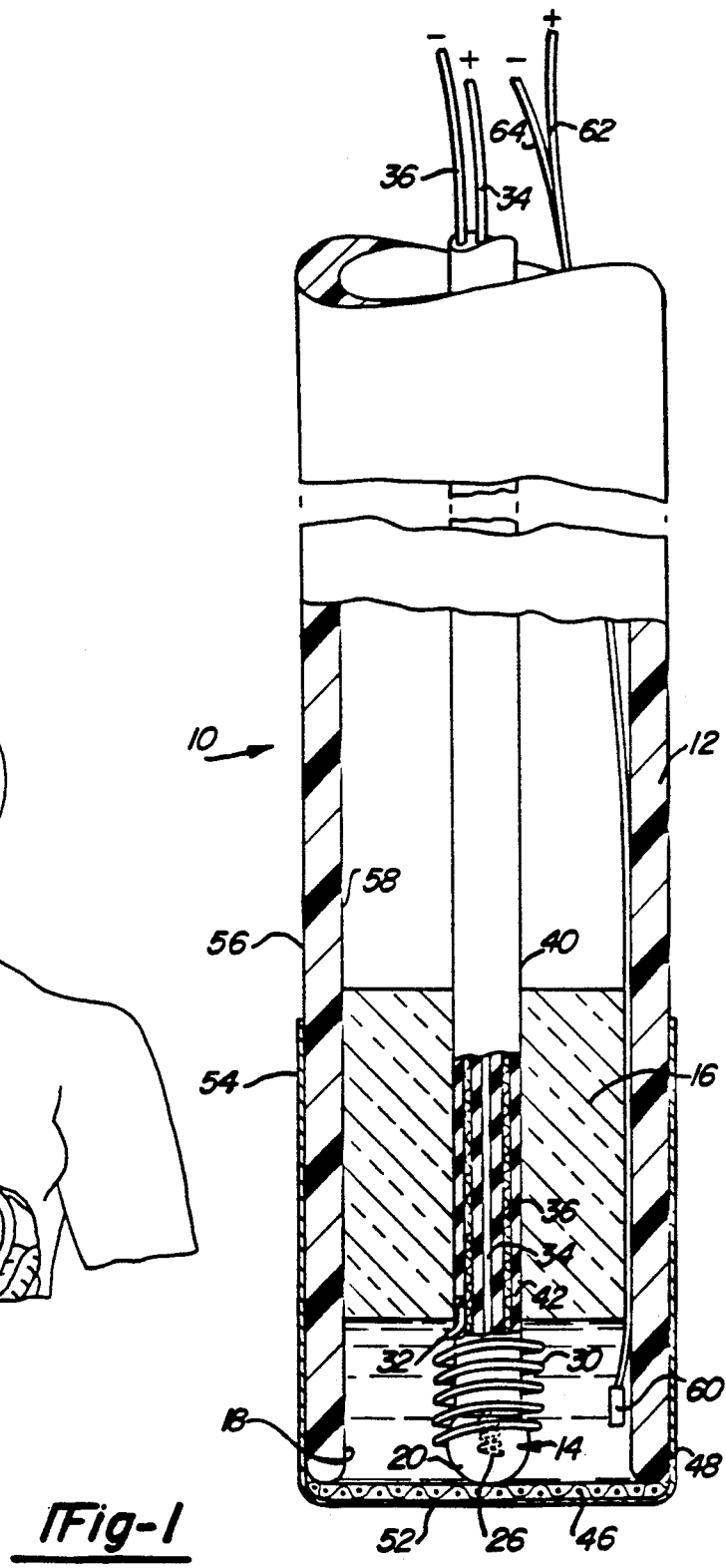

MINIATURE PCO₂ PROBE FOR IN VIVO BIOMEDICAL APPLICATIONS

BACKGROUND AND SUMMARY OF THE INVENTION

This invention relates to medical diagnostic equipment and methods and is particularly concerned with measurement of carbon dioxide in the body. The invention more particularly relates to an electrochemical $pCO_2$ sensor for making in vivo measurements.

A fall in the intramucosal pH may precede the development of intestinal ischemia and stress ulceration. The fall in pH in intestinal mucosa can be reliably calculated from a $pCO_2$ (partial pressure of $CO_2$) measurement using the Henderson-Hasselbalch equation. This is described in commonly assigned U.S. Pat. No. 4,643,192, entitled "Hollow Viscous Tonometry" and continuation applications Ser. Nos. 120,720 and 233,888 and in commonly assigned patent applications Ser. Nos. 237,287 and 380,706 entitled "Remote Sensing Tonometric Catheter Apparatus and Method," and in Ser. No. 237,286 entitled "Tonometric Catheter Combination," which are herein incorporated by reference.

In the above body of commonly assigned patent and applications certain techniques for sensing $pCO_2$ in vivo are described. Although semiconductor CHEMFET sensors and optical sensors are used, it would also be desirable to use electrochemical sensors for $pCO_2$ measurement. We have attempted to use conventional, commercially available electrochemical $pCO_2$ sensors and have found them to be generally inadequate. Conventional electrochemical $pCO_2$ sensors, based on the Severinghaus technology, are not sufficiently miniaturized or constructed for use in vivo do not give accurate readings unless properly oriented. For example, many electrochemical $pCO_2$ sensors work properly only when physically oriented upright. They do not work properly when oriented on the side or upside down.

Addressing the needs of the biomedical community, the present invention overcomes the shortcomings of the prior art electrochemical $pCO_2$ sensor technology. The present invention provides a miniaturized $pCO_2$ sensor of the electrochemical type. The sensor is well adapted for actual insertion through an appropriate orifice into a hollow organ for in vivo $pCO_2$ measurement. The probe comprises a selectively permeable first membrane which defines a closed reference chamber. A first electrode is disposed in the reference chamber. The first membrane is preferably a bulb-like glass membrane which is permeable to $H^+$ ions. A hollow flexible tube has a fluid tight plug inserted fully into one end leaving a test chamber space between the plug and the open end. An end cap comprising a selectively permeable second membrane is fitted over the open end to define a closed test chamber between end cap and plug. Preferably the second membrane comprises a silicone rubber which is permeable to $CO_2$ molecules.

The first membrane, with first electrode enclosed, is disposed within the test chamber. A second electrode is disposed in the test chamber in proximity to the first membrane. Preferably the second electrode is wrapped about the bulb-like first membrane structure adjacent the first electrode. The reference chamber is filled with a first electrolyte of known $H^+$ ion concentration. HCl may be used for this purpose. The test chamber is filled with a second electrolyte preferably including bicarbonate ions. The test chamber and reference chamber are both of such a size, and the respective electrolytes are of such a volume, that the respective electrolytes remains in contact with the corresponding electrodes over all spatial orientations of the probe. In other words, even when inserted through a body orifice, as in the case of a naso-gastric measurement, both electrodes remain in proper contact with their respective electrolytes, regardless of probe orientation. Accurate results are achieved whether the probe is right side up, upside down, or somewhere between.

The probe construction of the invention is well adapted to miniaturization and the probe can be in the form of an elongated tube of sufficient length and diameter to permit the tube to be slidably inserted through the channel of a nasogastric tube, an endoscope, or the like. Also, if desired, a thermistor temperature sensor can be incorporated in the probe to give a reading of core temperature at the $pCO_2$ probe site, and allow the $pCO_2$ reading to be corrected for temperature.

Further according to the invention, the $pCO_2$ probe comprises a flexible and noncollapsible hollow tube which has an open end that defines inner and outer sidewalls. A containment structure for defining a closed reference chamber is coaxially disposed within the hollow tube. The containment structure comprises a selectively permeable glass membrane portion which is adjacent to the open end of the hollow tube, and a carrier portion extending axially within the hollow tube. A supporting and sealing means is disposed in the hollow tube, in sealing contact with the inner sidewall to support the carrier portion of the containment structure. The first electrode has a portion disposed in the reference chamber and a portion which extends through and is supported by the carrier means. The reference chamber is substantially filled with a first electrolyte of known $H^+$ ion concentration.

A second electrode has a portion disposed concentrically around the glass membrane portion. The second electrode further has a portion extending through the supporting and sealing means. An end cap, comprising a second membrane selectively permeable to $CO_2$, is carried by the outer sidewall of the tube, in sealing contact therewith. The end cap thereby defines a fluid tight electrolyte chamber within the tube. The fluid tight chamber so defined thereby also contains the glass membrane portion.

The end cap has a radially extending planar or curved end face with a longitudinally extending cylindrical sidewall. The cylindrical sidewall is orthogonal to the end face. The end cap is elastically held in place by tensile forces of the end face which urge the cylindrical sidewall into contact with the outer sidewall of the hollow tube. The electrolyte chamber is substantially filled with a second electrolyte capable of changing pH in response to changes in $CO_2$ concentration.

For a more complete understanding of the invention and its objects and advantages, reference may be had to the following specification and to the accompanying drawings.

BRIEF DESCRIPTION OF DRAWINGS

FIG. 1 is a fragmentary cross-sectional view of a presently preferred $pCO_2$ sensor in accordance with the invention;

FIG. 2 is a diagram exemplifying one use of the $pCO_2$ sensor of the invention;

DESCRIPTION OF THE PRESENTLY PREFERRED EMBODIMENTS

Figure 3:
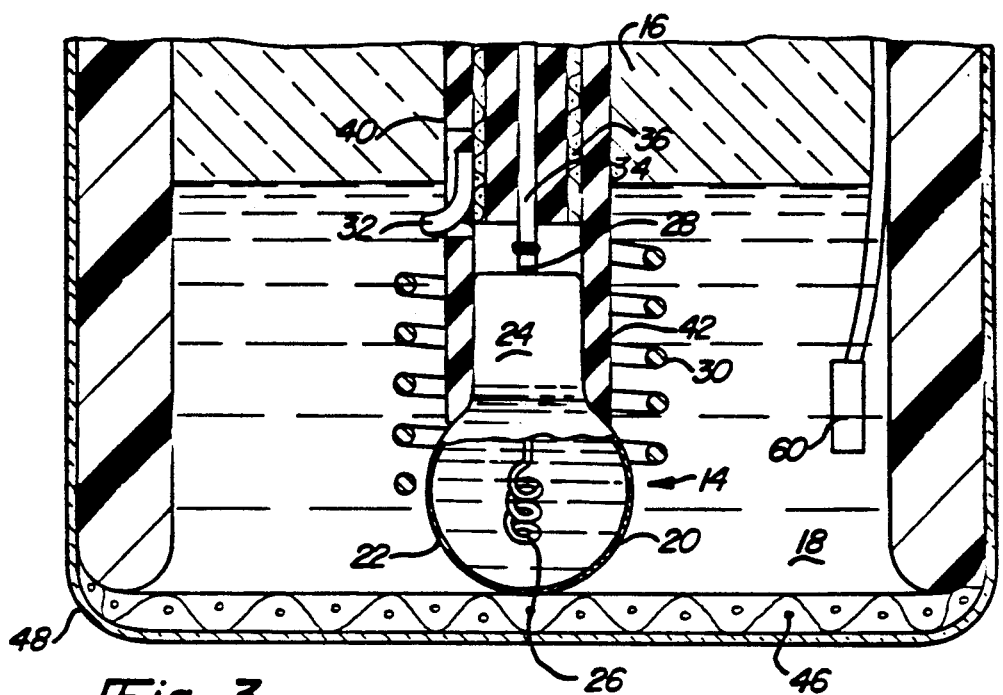
FIG. 3 is an enlarged fragmentary cross-sectional view of the pH sensor with helically wound second electrode also illustrated in FIG. 1.

Referring to FIG. 1, the $pCO_2$ probe is shown generally at 10. The probe comprises a flexible, noncollapsible hollow tube 12. Preferably constructed of polyethylene tubing. A suitable tubing of 2.92 mm inner diameter and 3.73 mm outer diameter is available from Clay Adams, a division of Becton Dickinson & Company, Parsippany, NJ 07054, under the Intramedic brand name. A pH probe 14, such as an esophageal probe Model MI-405-E available from Microelectrodes, Londonderry, NH, is coaxially arranged within tube 12 and held in place by silicone plug 16 approximately ½ inch in length. Silicone surgical tubing available from Dow Corning, Midland, MI, 48640, may be used for plug 16. Plug 16 is inserted into the end of tube 12, leaving a space which defines an electrolyte test chamber 18. Also see FIG. 3.

The pH probe 14 may comprise a selectively permeable glass membrane 20 Which is fashioned to include an enlarged bulb-like structure 22 and an elongated carrier portion 24. Disposed within glass membrane 20 is a first electrode 26 which includes a lead 28 that extends through and is supported by the carrier portion. A second electrode 30 is helically wound concentrically about glass membrane 20 and includes a lead 32. Second electrode 30 may be fabricated from a 3 inch length of silver wire, available from Microelectrodes, Londonderry, NH. Electrode 30 is electroplated in HCl to add a coating of AgCl.

Leads 28 and 32 are connected respectively to the center conductor 34 and shield conductor 36 of a coaxial cable 40. The plastic jacket 42 may extend beneath a portion of second electrode 30 to contact the bulb-like structure 22, offering it more structural support. Coaxial cable 40 extends the entire length of tube 12 to provide conductors 34 and 36 for connection to measuring instruments. The pH probe depicted has a 1.6 mm diameter glass bulb and includes a 3 m long coaxial cable of 1.4 mm outer diameter. Other pH probe sizes may also be used to practice the invention.

The glass membrane 20 is fully sealed about lead 28 to define a hollow interior which is filled with a first electrolyte of known $H^+$ ion concentration. The glass from which membrane 20 is fabricated is permeable to $H^+$ ions.

Figure 4:
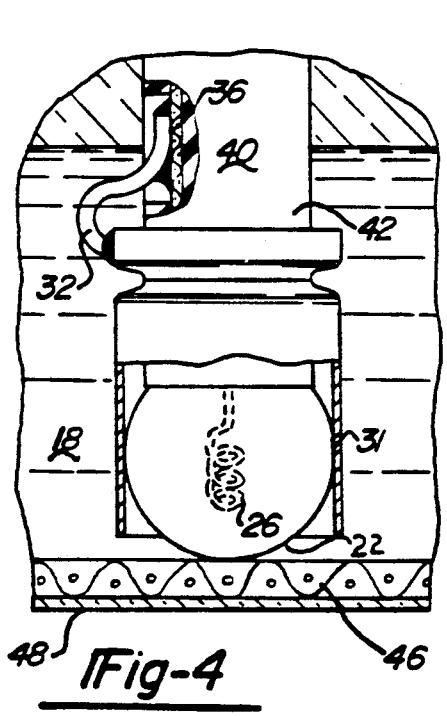
FIG. 4 is a similar enlarged fragmentary view of an alternate embodiment employing a cylindrical tube-like second electrode.

The details of one embodiment of electrode configuration are illustrated in FIG. 3. In this embodiment, the second electrode comprises a silver wire helically wrapped around the bulb-like structure 22. In the alternative, the helically wound wire electrode may be replaced with a cylindrical silver tube. This is illustrated in FIG. 4. The silver tube defines a second electrode 31. The tube may be crimped onto the end of the coaxial cable 40, with electrical connection made between the tube and the shield conductor 36. In both embodiments the silver second electrode is electroplated in hydrochloric acid to form a coating of AgCl. The electroplating may be done by filling the electrolyte test chamber 18 with hydrochloric acid and by temporarily inserting an electroplating electrode into the hydrochloric acid and applying an appropriate electroplating voltage between the electroplating electrode and the silver second electrode. In the presently preferred embodiment, this electroplating technique is accomplished using pure, undiluted HCl and a voltage source of about 2 volts in series with a 1K ohm resistor to limit current. The cathode is connected to the second electrode and the anode is placed in the HCl for approximately 5 minutes. During this time the current is initially about 500 mA, falling to about 100 microamperes at completion.

A nylon mesh spacer 46, available from Dow Corning's blood gas analyzer electrode maintenance kit, is positioned over the open end of tube 12, in contact with the extreme end of bulb-like structure 22. An end cap 48 of silicone rubber or other suitable $CO_2$ permeable material is frictionally fit onto the end of tube 12 to seal the electrolyte test chamber 18. The silicone rubber end cap may be constructed from the tip end portion of a clinical tonometer balloon, available from Speciality Manufacturing Company, Saginaw, MI 48603. Other suitable materials include Teflon ® and Tefzel ®, both available from DuPont. Chamber 18 is filled with a second electrolyte containing bicarbonate ions. The preferred second electrolyte formulation comprises a mixture of 0.06 M $KHCO_3$; 3 M KCl; saturated with AgCl and a mold inhibitor, such as available from Dow Corning for use with the Dow Corning blood gas analyzer. End cap 48 forms a membrane which is permeable to $CO_2$. The end cap includes a radially extending planar or curved end face 52 and longitudinally extending cylindrical sidewall 54. The sidewall is generally orthogonal to the end face and the end cap is elastically held in place by tensile forces of the end face urging the cylindrical sidewall into contact with the outer sidewall 56 of tube 12.

In manufacturing the $pCO_2$ probe of FIG. 1, the pH probe is positioned inside tube 12 by first pulling the pH probe through plug 16 and then pulling the plug and probe assembly through the open end of tube 12 into frictional sealing contact with inner sidewall 58. In the alternative, the pH probe may be temporarily held in position with plug 16 being poured in a molten state and then hardened. Chamber 18, formed by leaving space at the end of plug 16, is then filled with the second electrolyte by orienting the tube with open end facing up and filling with a syringe. Next the nylon mesh spacer 46 is placed onto the rim of the open end of tube 12 where it adheres by cohesion. The spacer is used to ensure that the entire bulb-like structure 22 is at all times covered with electrolyte after assembled for use. The spacer prevents the end face 52 of the end cap from contacting the bulb-like structure 22.

Next, the end cap is held open side up and filled to the brim with the second electrolyte. In order to ensure a tight fit, the end cap may be placed in a freon-based solvent prior to filling with electrolyte. The solvent causes the silicone end cap to expand, making it easy to slide onto the tube 12. With end cap held open side up, the tube 12 with pH probe and spacer installed is pressed into the end cap. Electrolyte spills over the rim of the end cap as the pH probe displaces the electrolyte. In this way no air bubble is trapped in the test chamber. With end cap installed, the freon is then permitted to evaporate from the silicone end cap material, whereupon the end cap shrinks to its original size and forms a tight, elastic fit.

If desired, a thermistor 60 may be positioned in the test chamber 18, with leads 62 and 64 extending through tube 12 for connection to suitable measurement equipment. A suitable thermistor is the Alpha NTC Micro-Thermistor (10 K ohms at 25° C.) available from Alpha Thermistor, Inc., San Diego, CA 92121. The leads 62 and 64 may be 0.028 inch outer diameter microminiature medical grade cable, available from Cooner Wire Co., Chatsworth, CA, 91311.

FIG. 2 illustrates one example of the $pCO_2$ probe in use as a naso-gastric measurement instrument. As illustrated, the operative end 66 of probe 10 is positioned in the hollow organ (in this case the stomach) where measurement is desired. The spatial orientation of the operative end is not of concern to the physician, since the probe will operate at all spatial orientations. This is attributed to the fact that both the glass membrane 20 and the electrolyte test chamber 18 are filled with a sufficient volume of the respective electrolytes so that the first and second electrodes remain in contact with the electrolyte at all orientations.

In constructing the probe to work at all spatial orientations, care is taken to prevent air bubbles from remaining in the test chamber 18 and in the glass membrane 20 over the anticipated operating temperature and pressure ranges. The $pCO_2$ probe can be made at any desired length to match the intended use. The non-inserted end can be provided with a fitting such as fitting 68, which electrically couples to conductors 34, 36, 62 and 64. Connecting cables 70 are then used to connect the $pCO_2$ probe and temperature sensor to the $pCO_2$ and temperature measurement equipment 72 and 74.

Figure 5:
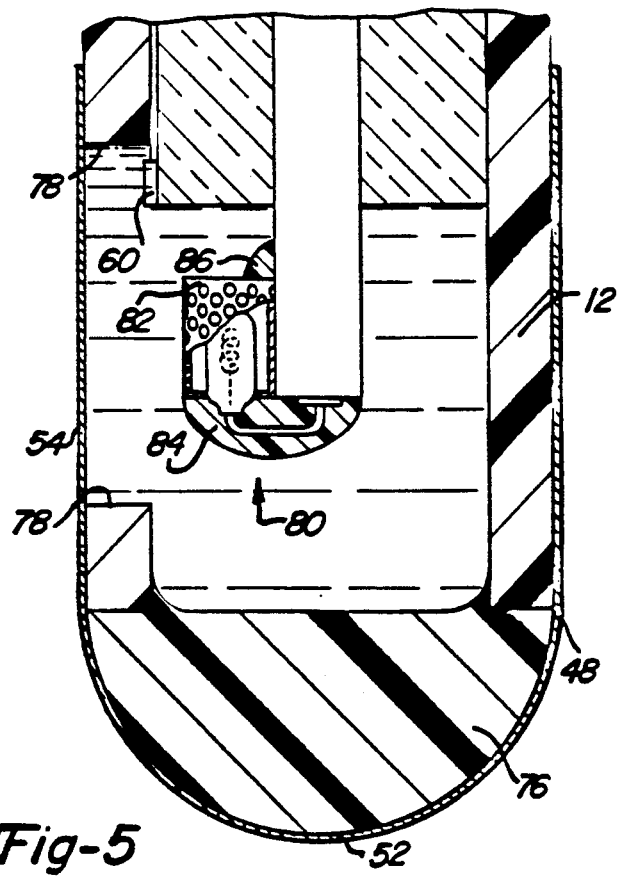
FIG. 5 is a fragmentary cross-sectional view of an alternate preferred $pCO_2$ sensor with side port.

An alternate embodiment of $PCO_2$ probe is illustrated in FIG. 5. The embodiment of FIG. 5 differs from the embodiment of FIG. 1 in that the end of tube 12 is heat and/or solvent sealed and may include a silicone rubber tip 76. A side port 78 is cut in the sidewall of tube 12 and the pH probe is configured as illustrated generally at 80 to have a side-looking characteristic. End cap 48 extends over the plastic filler 76 and also over the side port 78, as illustrated. If desired, a thermistor 60 may be included.

The side-looking pH probe 80 ma be provided with a perforated silver tubular second electrode 82. The pH probe assembly may be held in place on the side of the jacket 42 of coaxial cable 40 with suitable glue as at 84 and 86. Like the probe of FIG. 1, the alternate, side port construction of FIG. 5 is also made so that both electrodes remain properly covered with electrolyte at all spatial orientations. Care is taken to prevent air bubbles from being trapped in the electrolyte chambers.

Probe Calibration

Before use, and periodically during use the probe should be calibrated using a calibration solution of known $CO_2$ concentration. This may be done using ex-vivo automated calibration equipment of the type used to calibrate blood gas analyzers. Once the probe has been positioned in the body it may need to be retracted in order to calibrate. Although the probe is flexible enough to permit it to be retracted for calibration and then reinserted, retraction can be facilitated by fashioning the tonometric catheter with a suitable channel or conduit to slidably receive and guide the probe during insertion and retraction.

Figure 6:
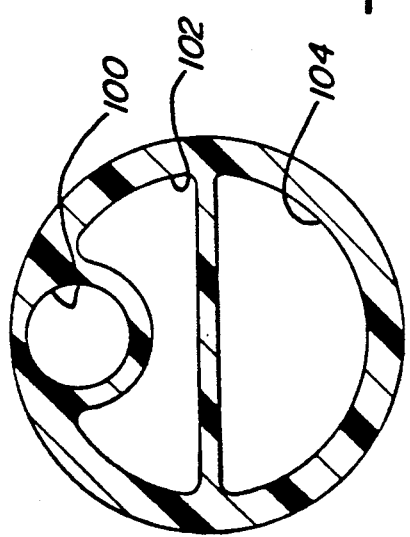
FIGS. 6 and 7 illustrate exemplary naso-gastric tubes in cross section, each with channel for receiving the $pCO_2$ sensor of the invention.
Figure 7:
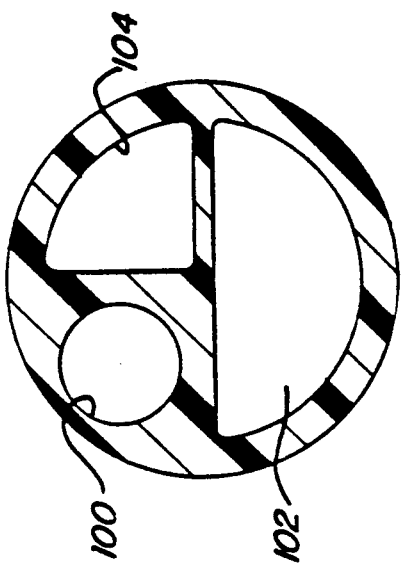
Figure 8:
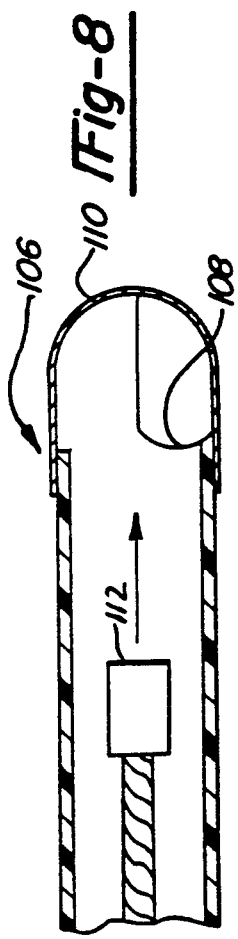
FIGS. 8 and 9 illustrate an exemplary naso-gastric tube in combination with a probe such as the $pCO_2$ sensor of the invention, showing one apparatus and method for probe calibration.
Figure 9:
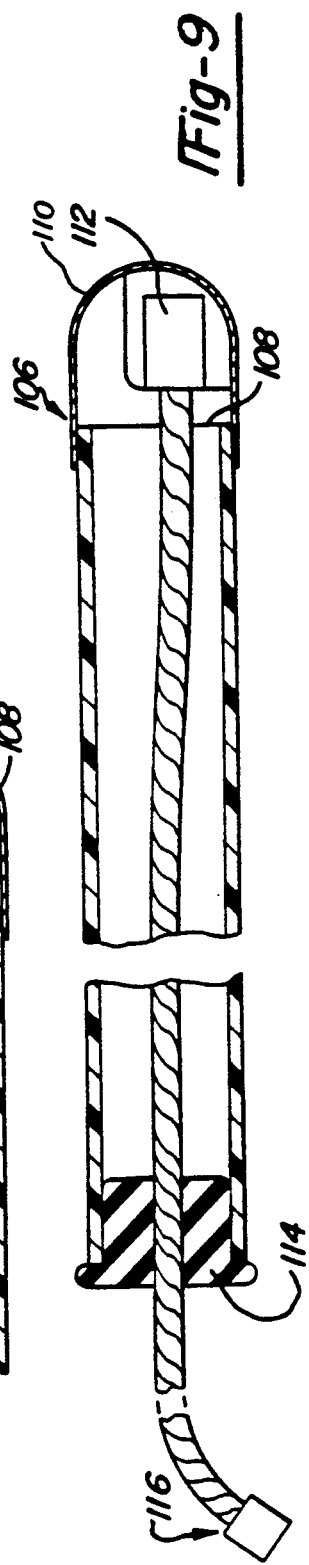

FIGS. 6 and 7 are examples of two different naso-gastric tubes, shown in cross section, which have been adapted to include a Sensor channel 100 in addition to the usual suction 102 and vent 104 channels or lumen. As illustrated in FIGS. 8 and 9, the tube tip 106 (in this case a naso-gastric tube) is provided with an appropriate window 108 covered by a silicone rubber or other permeable membrane 110. To insure that the operative end 112 of the probe is properly positioned in the window, a rubber stopper 114 is placed over the probe at the connector end 116. The stopper is positioned prior to insertion of the naso-gastric tube, with care being taken that the probe is properly positioned in the window 108 when the stopper is pressed into the non-working end of the tube. The stopper fits snugly about the probe body and thereafter acts as a stop or guide to aid in registration of probe tip and window, even while the naso-gastric tube remains in place within the body.

As an alternative to retraction and full calibration of the probe, it is possible to readjust the probe calibration to compensate for drift without removing it. This is done by using the tube (in this example a naso-gastric tube) to extract a fluid sample from the body and thereafter to measure the sample's $pCO_2$. Using the measured sample reading and making the assumption that the $pCO_2$ at the probe site matches that of the extracted sample, the probe calibration setting may be adjusted.

From the foregoing it is seen that the $pCO_2$ probe of the invention is well adapted for biomedical applications where in vivo measurements are indicated. While the invention has been described in connection with the presently preferred embodiments, certain modification's can be made to the structure and certain changes can be made to the selection of materials used, without departing from the spirit of the invention as set forth in the appended claims.

We claim:

1. A $pCO_2$ probe comprising:
   a selectively permeable first membrane defining a closed reference chamber;
   a first electrode disposed in said reference chamber;
   said first membrane comprising a fully sealed glass bulb at least partially enclosing said first electrode in said reference chamber and said first electrode including a conductor extending outwardly from said glass bulb;
   a hollow flexible tube having a fluid tight plug means and end cap means for defining a closed test chamber, said end cap means comprising a selectively permeable second membrane;
   said first membrane being disposed within said test chamber adjacent said end cap;
   a second electrode disposed in said test chamber about said first electrode and adjacent said end cap and in proximity to said first membrane;
   a first electrolyte of predetermined ion concentration contained in said reference chamber and in contact with said first electrode;
   a second electrolyte contained in said test chamber;
   said test chamber being of such a size and said second electrolyte being of such a volume that said second electrolyte remains in contact with said second electrode over all spatial orientations of said probe.

2. The probe of claim 1 wherein said first membrane is permeable to $H^+$ ions.

3. The probe of claim 1 wherein said end cap means is of silicone rubber.

4. The probe of claim 1 wherein said end cap means is elastically held on said tube.

5. The probe of claim 1 wherein said second membrane is of silicone rubber.

6. The probe of claim 1 wherein said second membrane is permeable to $CO_2$ molecules.

7. The probe of claim 1 wherein said first electrolyte, said reference chamber and said first electrode comprise a pH electrode.

8. The probe of claim 1 wherein said first electrolyte has a known concentration of $H^+$ ions.

9. The probe of claim 1 wherein said second electrolyte includes $HCO_3$.

10. The probe of claim 1 wherein said tube is elongated and flexible and wherein said conductor extends along the interior of said tube for electrically coupling a measurement device to said first electrode.

11. The probe of claim 1 wherein said tube is of a diameter to permit said tube to be slidably inserted through the channel of an endoscope.

12. The probe of claim 1 wherein said reference chamber is of such a size and said first electrolyte being of such a volume that said first electrolyte remains in contact with said first electrode over all physical orientations of said probe.

13. The probe of claim 1 further comprising temperature sensing means disposed in said test chamber for measuring the temperature of said second electrolyte.

14. The probe of claim 1 further comprising thermistor sensor disposed in said test chamber for electrically measuring the temperature of said second electrolyte.

15. A $pCO_2$ probe comprising:

a flexible and noncollapsible hollow tube having an open end and defining inner and outer sidewalls;

a containment means for defining a closed reference chamber coaxially disposed within said hollow tube, said containment means comprising a selectively permeable glass membrane portion forming a fully sealed glass bulb adjacent said open end of said hollow tube and a carrier portion extending axially within said hollow tube;

supporting and sealing means disposed in said hollow tube in sealing contact with said inner sidewall and supporting said carrier portion;

a first electrode having a portion disposed in said reference chamber within said glass bulb and a portion extending through and being supported by said carrier portion;

said reference chamber being substantially filled with a first electrolyte of known $H^+$ ion concentration;

a second electrode having a portion disposed concentrically around said glass membrane portion and having a portion extending through said supporting and sealing means;

end cap means comprising a second membrane selectively permeable to $CO_2$ carried by and in sealing contact with the outer sidewall of said tube to define a fluid tight electrolyte chamber within said tube and containing said glass membrane portion;

said end cap means having a radially extending end face with longitudinally extending cylindrical sidewall orthogonal to said end face, said end cap being elastically held in place by tensile forces of said end face urging said cylindrical sidewall into contact with said outer sidewall of said tube;

said electrolyte chamber being substantially filled with a second electrolyte capable of changing pH in response to changes in $CO_2$ concentration.

* * * * *

UNITED STATES PATENT AND TRADEMARK OFFICE
CERTIFICATE OF CORRECTION

PATENT NO. : 5,158,083

DATED : October 27, 1992

INVENTOR(S) : Emilio Sacristan, et al.

It is certified that error appears in the above-identified patent and that said Letters Patent is hereby corrected as shown below:

Column 3, line 36, "Which" should be --which--.

Column 5, line 40, "PCO$_2$" should be --pCO$_2$--.

Column 5, line 50, "ma" should be --may--.

Signed and Sealed this

Thirty-first Day of May, 1994

*Attest:*

BRUCE LEHMAN

*Attesting Officer*     *Commissioner of Patents and Trademarks*